US010007985B2

(12) United States Patent
Leon et al.

(10) Patent No.: US 10,007,985 B2
(45) Date of Patent: Jun. 26, 2018

(54) METHOD FOR THE AUTOMATIC SEGMENTATION AND QUANTIFICATION OF BODY TISSUES

(71) Applicants:Universidad de los Andes, Bogotá D.C. (CO); Hospital Universitario San Ignacio, Bogotá D.C. (CO); Hospices Civils de Lyon, Lyons (FR)

(72) Inventors: Ricardo Antonio Mendoza Leon, Bogotá D.C. (CO); Luis Felipe Uriza Carrasco, Bogotá D.C. (CO); Phillipe Charles Douek, Bron (FR); Marcela Hernández Hoyos, Bogotá D.C. (CO)

(73) Assignees: Universidad de los Andes, Bogota D.C. (CO); Hospital Universitario San Ignacio, Bogotá D.C. (CO); Hospices Civils de Lyons, Lyons (FR)

( * ) Notice: Subject to any disclaimer, the term of this patent is extended or adjusted under 35 U.S.C. 154(b) by 0 days. days.

(21) Appl. No.: 15/350,687

(22) Filed: Nov. 14, 2016

(65) Prior Publication Data

US 2017/0091935 A1    Mar. 30, 2017

Related U.S. Application Data

(63) Continuation of application No. PCT/CO2015/000009, filed on May 11, 2015.

(30) Foreign Application Priority Data

May 14, 2014    (CO) .................................. 14-103932

(51) Int. Cl.
*G06K 9/00*    (2006.01)
*G06T 7/00*    (2017.01)
(Continued)

(52) U.S. Cl.
CPC ............ *G06T 7/0012* (2013.01); *A61B 6/032* (2013.01); *A61B 6/5205* (2013.01);
(Continued)

(58) Field of Classification Search
None
See application file for complete search history.

(56) References Cited

U.S. PATENT DOCUMENTS

| 5,657,362 A * | 8/1997 | Giger .................... G06T 7/0012 378/37 |
| 2006/0204063 A1* | 9/2006 | Nakashima .......... G06T 7/0012 382/128 |

FOREIGN PATENT DOCUMENTS

WO    2007099525 A2    9/2007

OTHER PUBLICATIONS

Mendoza, Ricardo, et al. "Automatic segmentation of adipose viseral tissue from CAT images, employing anatomical invariants." Computing Congress (CCC), 2011 6th Colombian. IEEE, 2011. (translation of IDS submitted reference).*
(Continued)

*Primary Examiner* — Sean Conner
(74) *Attorney, Agent, or Firm* — Baker & Hostetler LLP

(57) ABSTRACT

A computer-based method is herein disclosed, allowing to differentiate automatically between two tissues of interest: an extrinsic and an intrinsic tissue, from a plurality of images, obtaining a quantitative assessment of each of said tissues without requiring the intervention of an expert. Said method involves the definition of a differentiation region in images obtained from a medical imaging acquisition device using a parametric contour, after which differentiation and quantification are carried out based on the photometric characteristics of the different tissues observed in images, evaluating the local neighborhood of each voxel belonging (Continued)

to the differentiation region previously defined in the plurality of images. The disclosed method increases to a great extent precision in differentiation and quantification of tissues, while the shown percentage error is considered tolerable for diagnostic purposes.

37 Claims, 21 Drawing Sheets

(51) Int. Cl.
    *G06T 7/11*     (2017.01)
    *A61B 6/03*     (2006.01)
    *A61B 6/00*     (2006.01)
    *G06K 9/46*     (2006.01)

(52) U.S. Cl.
    CPC .............. *G06K 9/4604* (2013.01); *G06T 7/11* (2017.01); *G06T 2207/10081* (2013.01); *G06T 2207/30004* (2013.01); *G06T 2207/30092* (2013.01); *G06T 2207/30242* (2013.01)

(56) References Cited

OTHER PUBLICATIONS

Ricardo Mendoza, et al., "Automatic Segmentation of Adipose Viseral Tissue From CAT Images, Employing Anatomical Invariants", Computing Congress (CCC), 2011 6th Colombian IEEE, May 4, 2011, pp. 1-6.
Jianhua Yao et al., "Fully Automated Adipose Tissue Measurement on Abdominal CT", Medical Imaging 2011: Biomedical Applications in Molecular, Structural, and Functional Imaging, SPIE, Mar. 3, 2011, vol. 7965, No. 1, pp. 1-6.
International Search Report for PCT/CO2015/000009, filed May 11, 2015.
Written Opinion for PCT/CO2015/000009, filed May 11, 2015.

\* cited by examiner

METHOD FOR THE AUTOMATIC SEGMENTATION AND QUANTIFICATION OF BODY TISSUES

CROSS REFERENCE TO PRIOR APPLICATIONS

This application is a continuation of International Application No. PCT/CO2015/000009, filed May 11, 2015 and designating the U.S., which claims priority to Colombian Patent Application No. 14-103.932, filed May 14, 2014, both of which are incorporated herein by reference in their entirety.

TECHNICAL BACKGROUND

Imaging is a discipline of medicine that uses different modalities of images of human body acquired by a set of equipment and methods to reach in a fast and reliable way the identification of diverse diseases.

Imaging comprises the making of all types of diagnostic and therapeutic exams in which equipment for reproducing images of the body are used, a specialty that has provided an unexpected contribution to the progress and development of health sciences. Nowadays different modalities of human body images are used, which are acquired by using a set of equipment and methods such as: ultrasound, computed axial tomography, nuclear magnetic resonance, conventional and digital radiology, for achieving in a fast and reliable way the identification of different diseases, becoming indispensable tools for the proper and qualified care of patients.

However, it is clear that the benefit obtained from imaging in favor of the health of patients largely depends on the ability of correctly interpret data provided by medical images, regardless of said interpretation is carried out by manual or direct methods (that is, by an expert) by interactive methods, by semi-automatic methods (those in which there is partial intervention of an expert and also computational techniques are applied) or by automatic methods (where the analysis is performed completely through computational techniques).

In addition, interpretation of medical images may include different objectives, including: i) measurement of any property of the input image, so that the result is a scalar or vector; ii) definition of an image as normal or abnormal without the need to identify a specific region within the image; and iii) division of an image into a set of different regions based on a similarity measure, in which case there may be a generic segmentation where the objective is to produce descriptions of the content of an image, or a segmentation that involves the detection and localization of all regions of an image that share a common characteristic.

However, specifically regarding segmentation and quantification of medical images by manual or direct methods, such task generally turns out to be wasteful and subject to inter and intra-observer variability, a fact that has motivated the development of several computational techniques for estimating and discriminating the area of different regions present in the images to be interpreted. However, the anatomical diversity of the patients affects the result of these methods, reason why the intervention of an evaluator is generally necessary to make corrections to the result, being very extensive in some cases, and therefore subtracting reliability for its diagnostic use.

On the other hand, interactive methods assist the expert in the differentiation task by facilitating the tracing of contours that define regions with exclusive content from one or another tissue to be differentiated (distinguished). In this group are found those methods requiring contours traced by an expert user to define the different regions of interest and where quantification is performed taking advantage of the contours given by the user and counting the voxels included within said contours. However, although these methods facilitate the work of the expert, the effort required is still significant and can skew his judgment.

Semi-automatic methods seek to differentiate the region of interest in the image using various schemes for detection of tissues and organs of interest, generally using segmentation global techniques such as ray tracing, region growing and deformable models. However, the existence of strange elements and dependency regarding certain particular anatomical characteristics make necessary the active intervention of the user.

For example, in the scientific paper by Romero et al (2006), a semi-automated detection technique of the external walls of the abdominal cavity for segmentation and differentiation between visceral adipose and subcutaneous tissue is disclosed. Such technique uses a specially designed threshold and two acceptance distance criteria between this, the skin and the intra-peritoneal region, further identifying the muscle tissue to avoid false positives. Unfortunately, said technique presents serious drawbacks when there are discontinuities in the contour of the abdominal region, and consequently the visceral adipose tissue is indistinguishable from the subcutaneous adipose tissue.

Also it is known in the state of the art the proposal by Zhao et al (2006) for detecting the contour of the abdominal internal region in volumetric tomography images, which is based on the creation of radial profiles (rays) from a point located at the geometric center of the rectangle containing the body, so these rays are explored, starting at the external contour of the body towards the center, until finding the first discontinuity corresponding to the adipose tissue, thereby obtaining a candidate contour point. Then, the radius of the candidate points is smoothed in order to correct distortion generated by strange elements such as calcifications and discontinuities in the abdominal internal contour.

In turn, the method proposed by Ohshima et al (2008) allows to detect the internal abdominal contour and the intra-peritoneal region contour using two centers of ray generation, fact that allows to evaluate visceral, subcutaneous and intra-muscular adipose tissue in a independently way on computed axial tomography images. However, as the authors themselves point out, said method has a high dependence on specific anatomical characteristics, being seriously affected by the presence of discontinuities in the internal abdominal contour.

On the other hand, patent application WO 2011/139232 discloses an automatic method for the identification of adipose tissue on a set of three-dimensional magnetic resonance images from the abdomen of a patient, and its subsequent segmentation into visceral and subcutaneous adipose tissue. Such method is based on the definition of two-dimensional or three-dimensional graphs with vertices corresponding to abdominal image voxels and edges connecting neighbor vertices.

However, the method disclosed in said reference uses a global approach (graph partitioning) for the differentiation of adipose tissue voxels, which is supported on the assumption of a minimum thickness of subcutaneous adipose tissue around the intra-peritoneal cavity and in the continuity of that region of adipose tissue, in a way that said region is unique and is delimited by a unique external contour and a unique internal (closed) contour. Such internal contour is of fundamental importance as it defines the initial partition to be used in the optimization of the graph partition. However, in cases where this assumption is not fulfilled, the method of graph partitioning critically fails with unpredictable results because the region of adipose tissue may be delimited by a single contour: the external, or even by a plurality of internal and external contours, preventing the proper selection of an initial partition. Although the disclosed method foresee the occurrence of this problem in cuts at navel height, does not have a mechanism to prevent this problem when the thickness of subcutaneous adipose tissue is particularly narrow and difficult to distinguish from the skin and musculature of the intra-peritoneal region. This weakness is aggravated by the fact that many cases of clinical importance are related to non-obese individuals with an unusually high distribution of visceral adipose tissue, where it is common to find places where the thickness of subcutaneous adipose tissue is minimal and almost imperceptible (much less than 5 mm). Additionally, the presence of strange elements in the abdominal region, as probes or calcifications, can lead to the existence of multiple internal regions within the subcutaneous region or even its fractionation into multiple connected regions (multiple external contours).

Finally, the scientific paper of Mendoza et al (2011) discloses a method to perform the segmentation and quantification of subcutaneous adipose tissue (SAT) and visceral adipose tissue (VAT) using computed axial tomography (CAT) images. This method uses the evaluation of local anatomical invariants on adipose tissue voxels, achieving their differentiation and quantification.

However, even though this document provides an overview of a computational method for segmentation and quantification of SAT and VAT, therein several factors that are necessary to obtain reliable data are not taken into account, including the following:

The differentiation between SAT and VAT tissues is performed over the entire area of the body, which leads to incorrect tissues differentiation due to incomplete removal of the skin after applying the operator of morphological opening, inducing errors during the evaluation of adipose tissue, especially when there are folds in the skin or acquisition artifacts resulting from patient movement;

A central voxel is labeled as visceral tissue only if the number of neighbor voxels labeled as visceral tissue in its neighborhood is greater than or equal to 6, which leads to underestimate the visceral tissue in places nearby to discontinuities of the intra-peritoneal contour;

The initial gap-filling is performed between the application of the morphological opening and closing operator, which increases the probability of filling the body region in an incomplete way, due to the nature of the morphological opening operator by opening regions defined by a closed contour The initial thresholding is performed using a range that includes only the adipose tissue, which prevents the correct segmentation of the region of the body, particularly when the differentiation of the subcutaneous tissue between the skin and the contour of the intra-peritoneal cavity is difficult, leading to the appearance of discontinuities in the external contour of the segmented subcutaneous tissue that consequently prevent completely recover the body region;

The neighborhood (denoted as M) on which the final SAT and VAT selection criteria are evaluated, has a size of 3×3, which provides insufficient information to accurately determine the type of adipose tissue to which the central voxel belongs, leading to incorrectly differentiate the tissues.

The initial gap-filling and the gap-filling stage where the radius of the traced rays is limited require as a condition, for labeling the voxel under evaluation, that all traced rays intercept an already segmented voxel, which prevents gaps with discontinuities in its contour to be completely filled in, excluding such tissue regions from differentiation.

Additionally, the document of Mendoza et al (2011) does not concretely describe key aspects such as the distribution and geometry of the rays, their initialization and termination conditions, the information that must be recorded during tracing, the way in which said recorded information must be processed at the end of rays tracing, as well as neither describes the cases, conditions and actions taken based on this.

In view of the above, it is clear that there is a persistent need in the state of the art to develop a computer implemented method that allows to automatically discriminate between two tissues of interest, from a plurality of images, being able to obtain a quantitative valuation of each of those tissues without requiring the intervention of an expert.

BASIC CHARACTERISTICS OF THE INVENTION

Now then, taking into account the teachings of the prior state of the art and based on methods for tissue differentiation and quantification from medical imaging heretofore known, the applicant of the present invention has developed a computer-implemented method for discriminating between two tissues of interest on a plurality of images, wherein said method comprises the following steps:
a) Establishing the parameters required to determine whether an area of the plurality of images corresponds to one or another tissue of interest;
b) Defining a differentiation region in said plurality of images; and
c) Differentiating between areas of the plurality of images belonging to each of the tissues of interest inside of the differentiation region defined in b).

The method of the invention enables to locally identify the type of tissue, for example, without requiring previous construction of the contours or user assistance, facts constituting it in an ideal mechanism for automatic segmentation and quantification of tissues from medical images.

Additionally, the method of the invention incorporates a series of tools allowing to reduce the misclassification of tissues that is generated as a result of factors such as skin folds, spinal muscles, intestinal contents, bone structure, among others.

DETAILED DESCRIPTION OF THE INVENTION

In addition to the previously outlined, the subject matter of the present application and the surprising technical advantages achieved by the inventor may be appreciated in detail by the subsequent description of the method for automatic segmentation and quantification of body tissues, making reference to the accompanying drawings, where:

Figure 4:
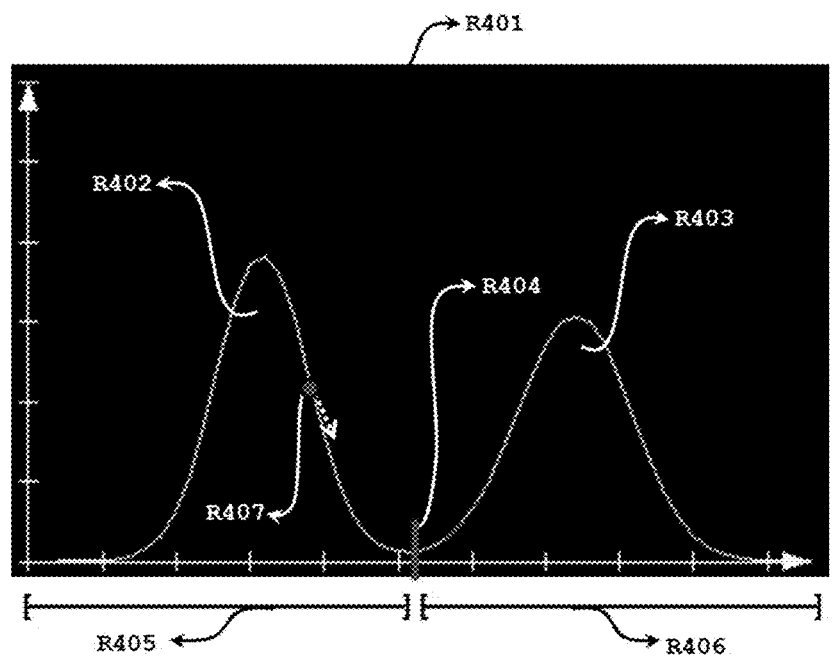

FIG. 4 provides a representation of a generic bi-modal histogram, and an example of the separation threshold with their respective ranges for each mode.

Figure 5A:
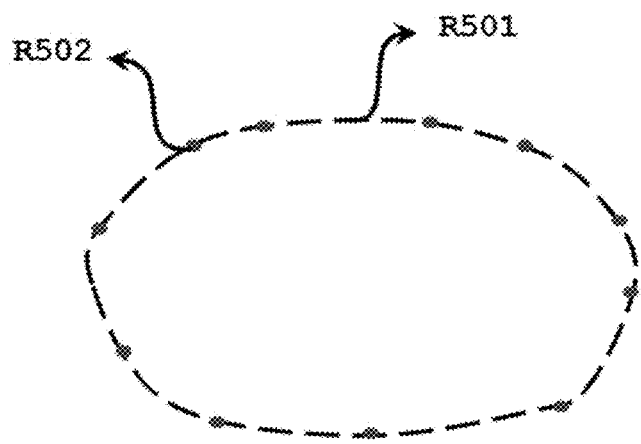

FIG. 5a shows the basic structure of a parametric contour and its control points.

Figure 5B:
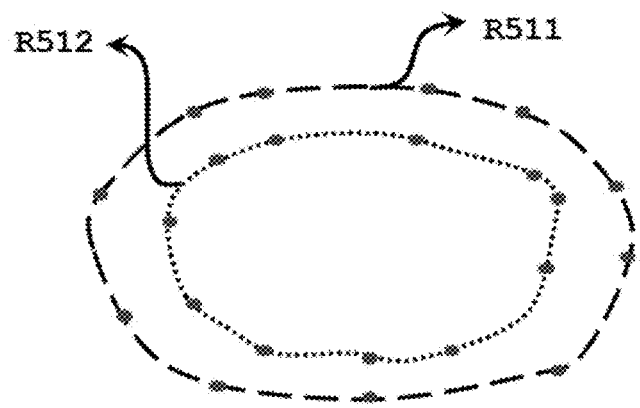

FIG. 5b illustrates the possible evolution of a parametric contour from an initial configuration to a final configuration in energy balance.

Figure 5C:
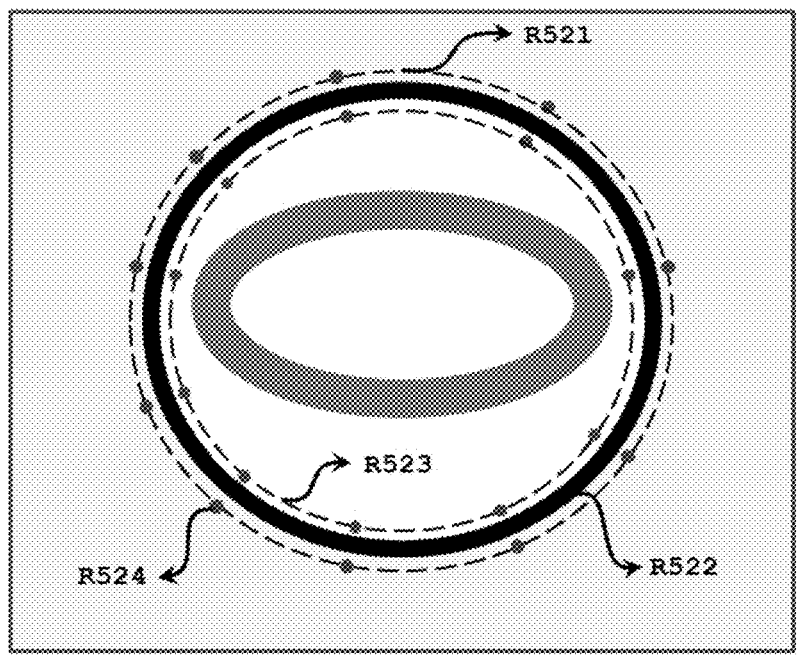

FIG. 5c illustrates possible alternatives to define the initial configuration of the parametric contour based on easily identifiable contours in an image.

Figure 5D:
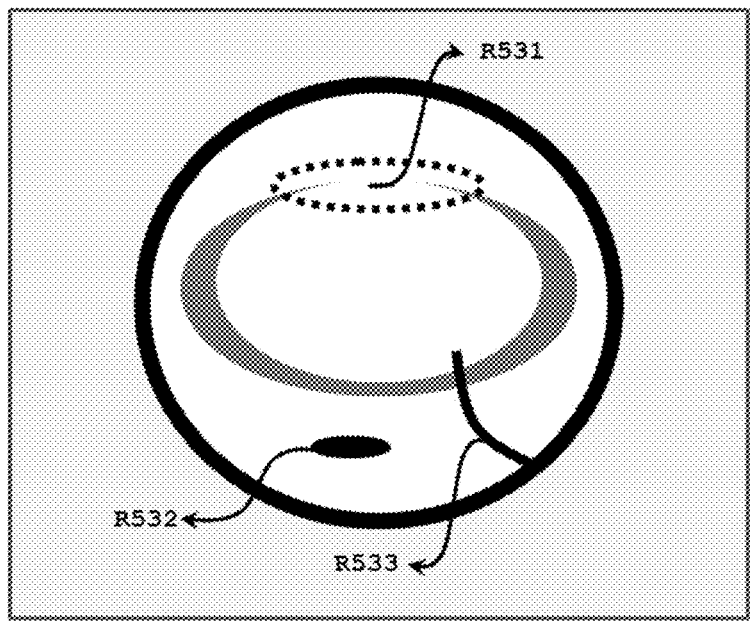

FIG. 5d presents different scenarios that can prevent proper differentiation of extrinsic and intrinsic tissues, such as discontinuities in the tissues and strange elements.

Figure 5E:
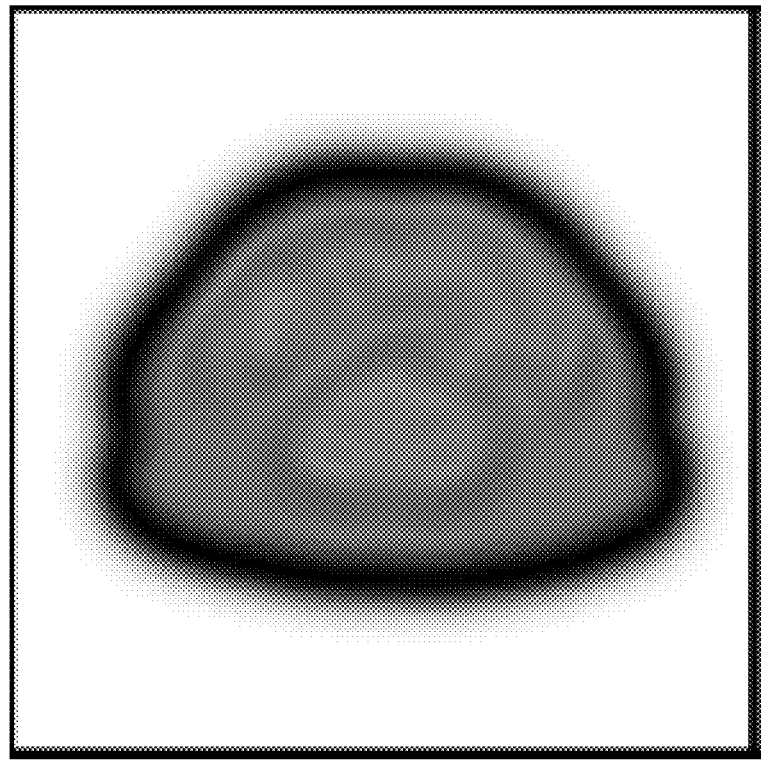
Figure 5F:
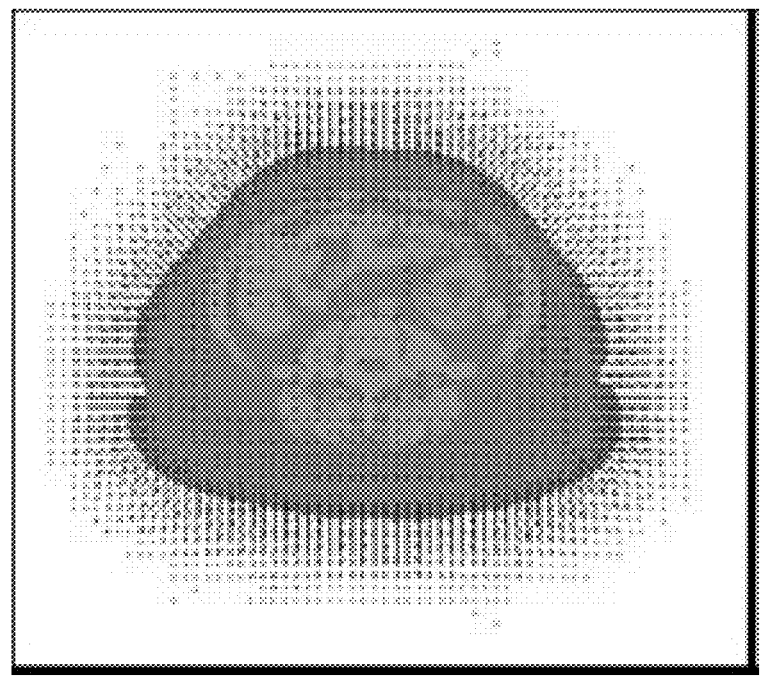

FIGS. 5e and 5f illustrate a pseudo-energy potential over an image and the vector field associated with such potential, respectively.

Figure 6:
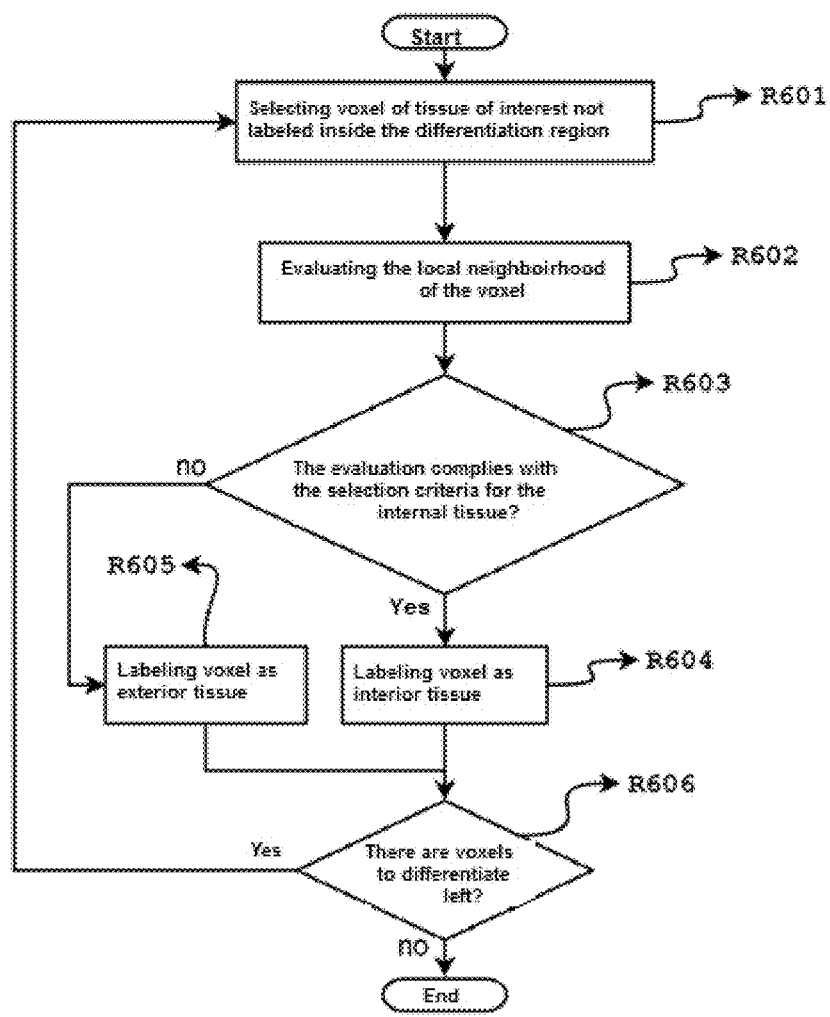

FIG. 6 shows the general flow chart of the differentiation of tissues of interest by local evaluation of neighborhoods.

Figure 7A:
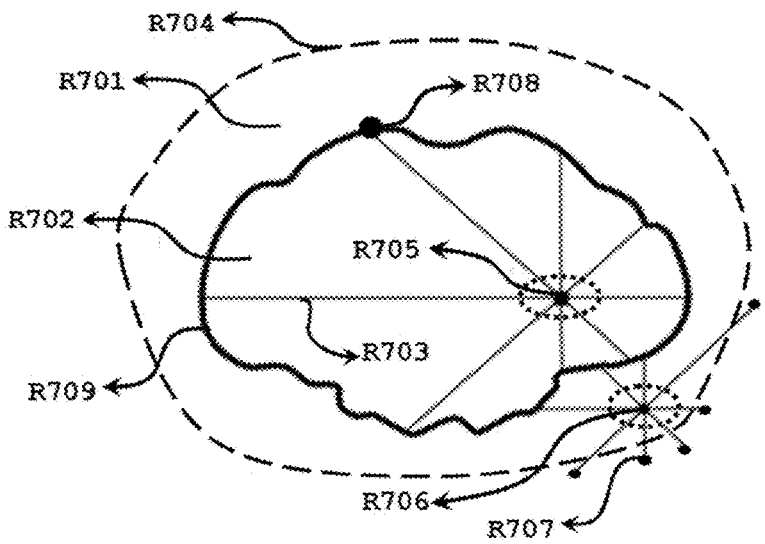

FIG. 7a shows a general diagram of the evaluation for the extrinsic and intrinsic tissues of interest through a ray tracing.

Figure 7B:
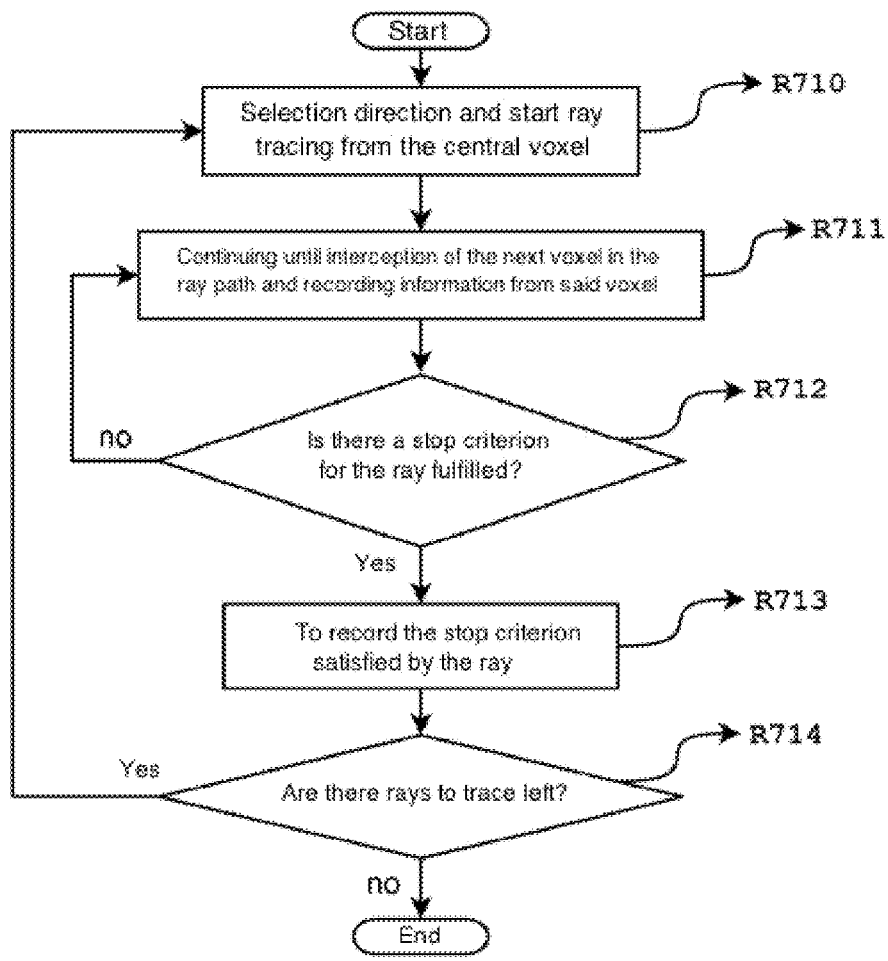

FIG. 7b shows the general flow chart describing the steps to be followed for tracing the rays and obtaining the information from the local neighborhood to a voxel.

Figure 7C:
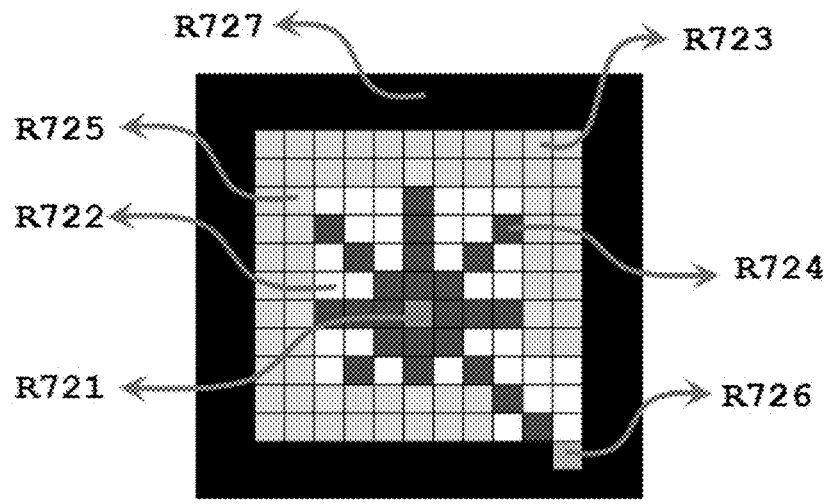
Figure 7D:
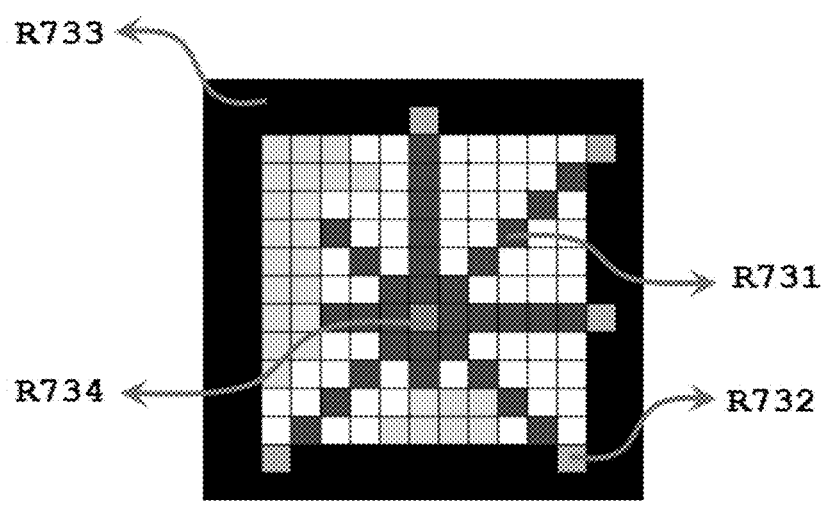
Figure 7E:
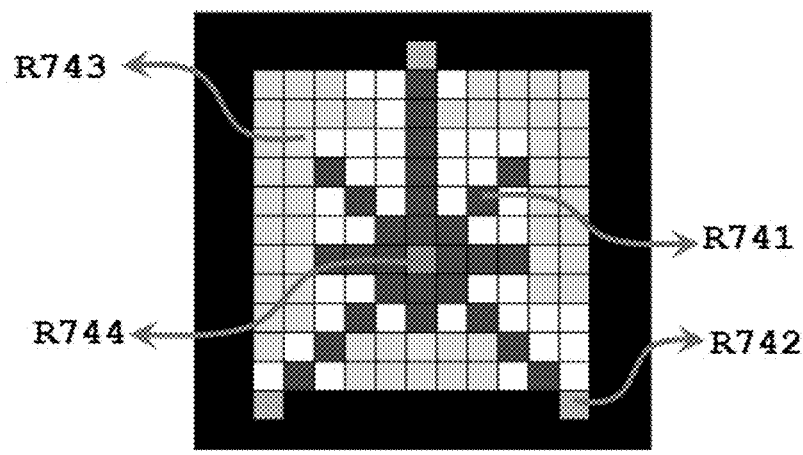

FIGS. 7c, 7d and 7e illustrate different cases of evaluation of ray tracing and the corresponding labeling of the central voxel.

Figure 7F:
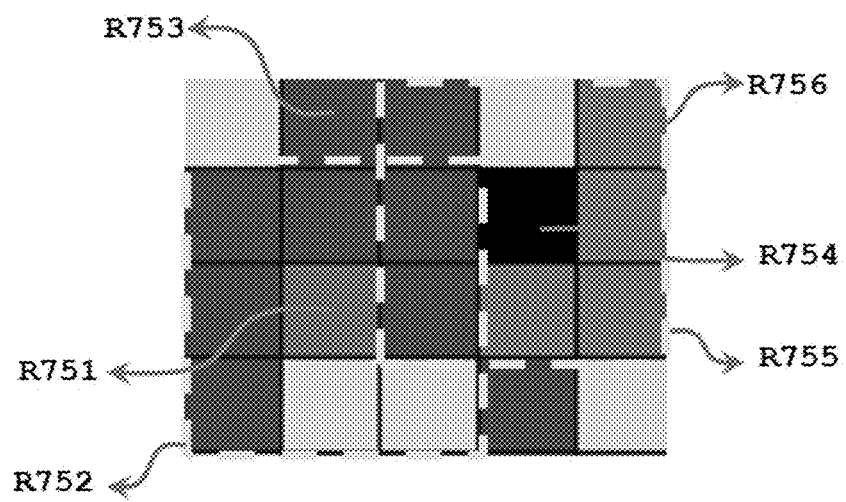

FIG. 7f shows an alternative for carrying out the final evaluation of the voxels labeled as indeterminate inside of a neighborhood.

Figure 8:
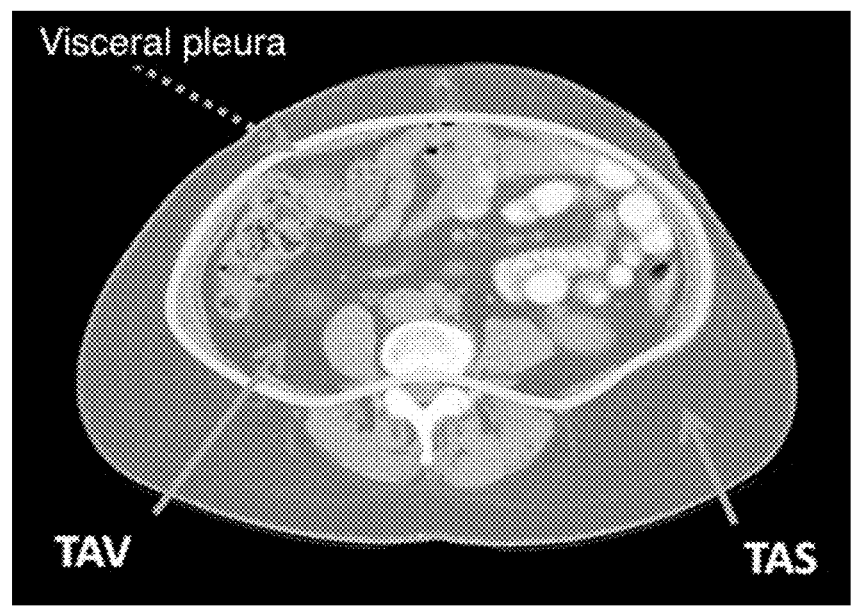

FIG. 8 shows an image of computed axial tomography of the abdomen where the regions corresponding to subcutaneous adipose tissue are identified as extrinsic tissue and visceral adipose tissue as intrinsic tissue, as well as the visceral cavity that anatomically delimits such tissue regions.

Figure 9:
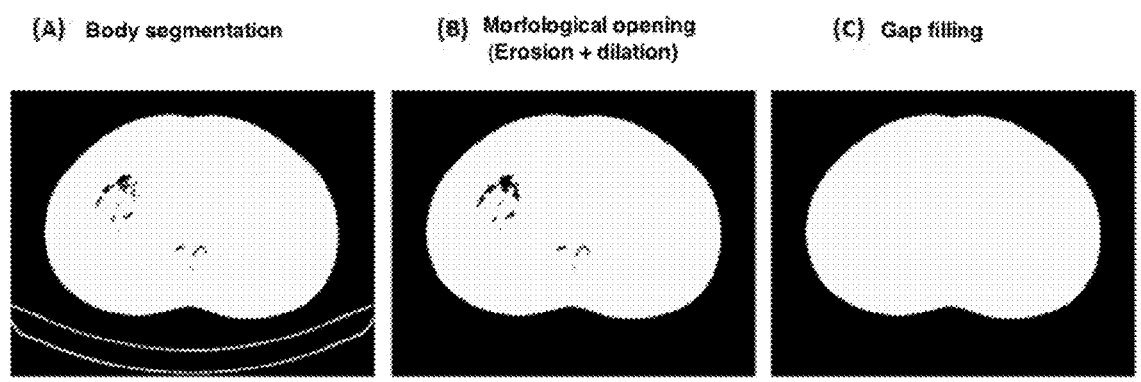

FIG. 9 shows the sequence of results during the removal of the abdominal region for a specific embodiment of the invention.

Figure 10:
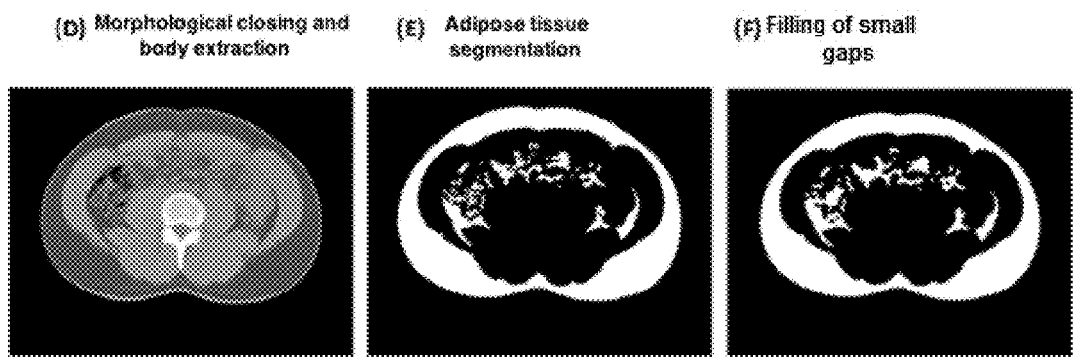

FIG. 10 shows the sequence of results during the segmentation of adipose tissue in the abdominal region for a specific embodiment of the invention.

Figure 11:
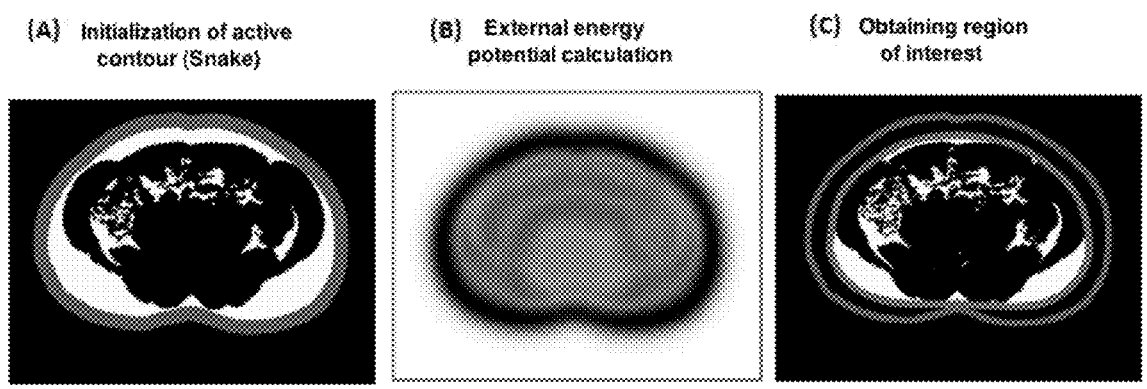

FIG. 11 shows the sequence of results during the definition of the differentiation region for a specific embodiment of the invention.

Figure 12:
Figure 12:
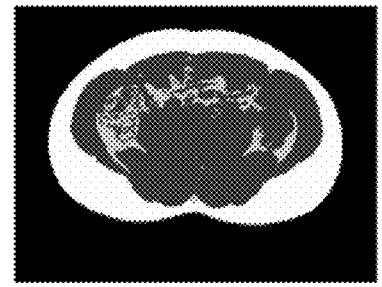

FIG. 12 shows the sequence of results during differentiation of the tissues of interest for a specific embodiment of the invention.

FIGS. 13a, 13b, 13c and 13d show diverse examples of final results of differentiation following a specific embodiment of the invention.

FIGS. 14a, 14b, 14c and 14d show a comparative example between the results obtained using a specific embodiment of the method, and the results obtained by using this specific embodiment but including additional screening steps.

Figure 1A:
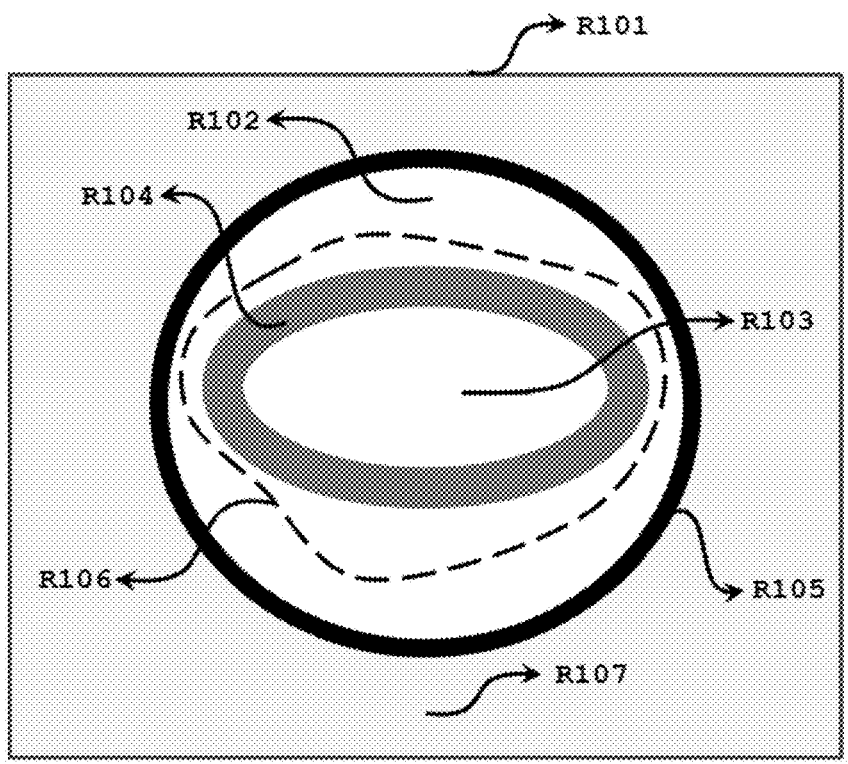
FIG. 1a shows a graphical representation of an image belonging to a plurality of images, and a generic configuration of the different regions of tissue among which extrinsic and intrinsic tissues are included.

FIG. 1a shows a graphical representation of an image R101 belonging to a plurality of images of the inside of a body, wherein said body is located inside of a background R107, wherein inside of said body are located two regions of tissues of interest to be differentiated: an extrinsic tissue R102 and an intrinsic tissue R103 that may or may not have different photometric characteristics distinguishing them, wherein region R102 is externally delimited by tissue R105 and inside by tissue R104 which in turn externally delimits the region R103. Such image R101 may correspond to a sequence of two-dimensional reconstructions of signals obtained by a medical image acquisition device, defining a plane over each one of them. On the other hand, tissue R104 may be continuous or present discontinuities, partially delimiting the tissue 103, which consequently would allow the contact of tissue R102 with tissue R103 at one or more locations. Likewise, the location of tissue R104 may be very close to that of tissue R105 and even being in contact. Finally, both the shape and the thickness of tissues R104 and R105 may vary along their length.

Figure 1B:
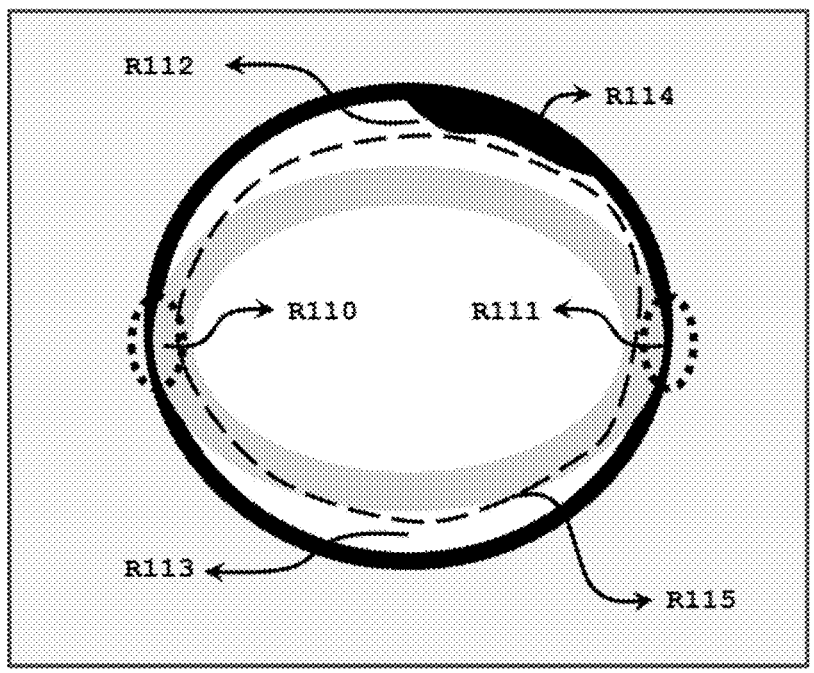
FIGS. 1b and 1c show alternative examples of the graphical representation of FIG. 1a, where situations increasing the difficulty of the problem that is subject matter of the invention may be noticed.
Figure 1C:
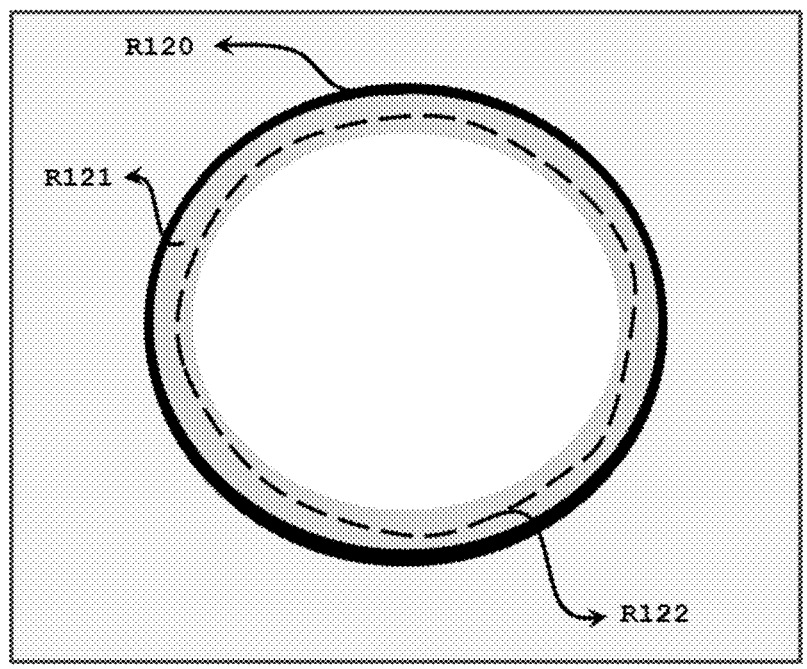

FIGS. 1b and 1c show alternative examples of the graphical representation of FIG. 1a, where situations that increase the difficulty of the objective problem of the invention may be noticed, for example, the binding of tissues R104 and R105 at locations R110 and R111 along its length, resulting in the division of the region of tissue R102 into two regions R112 and R113.

Figure 2:
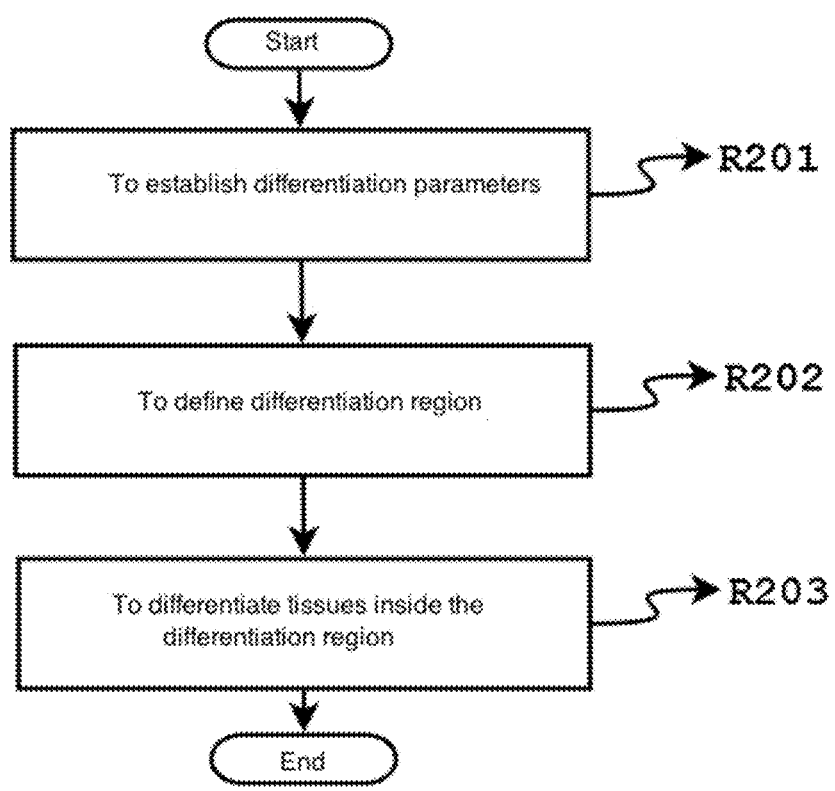
FIG. 2 shows the flow chart of the essential steps of the method of segmentation and quantification of body tissues.

FIG. 2 shows a general diagram of the three essential steps of the method: in step R201 the parameters to be used in the differentiation of extrinsic tissue R102 and intrinsic tissue R103 are set; in step R202, based on the image R101, it is defined a differentiation region bounded by the contour R106 containing the region R103 and that is located inside of the region bounded by the external contour of tissue R105; and step R203, where the differentiation of tissues R102 and R103 is carried out.

Figure 3:
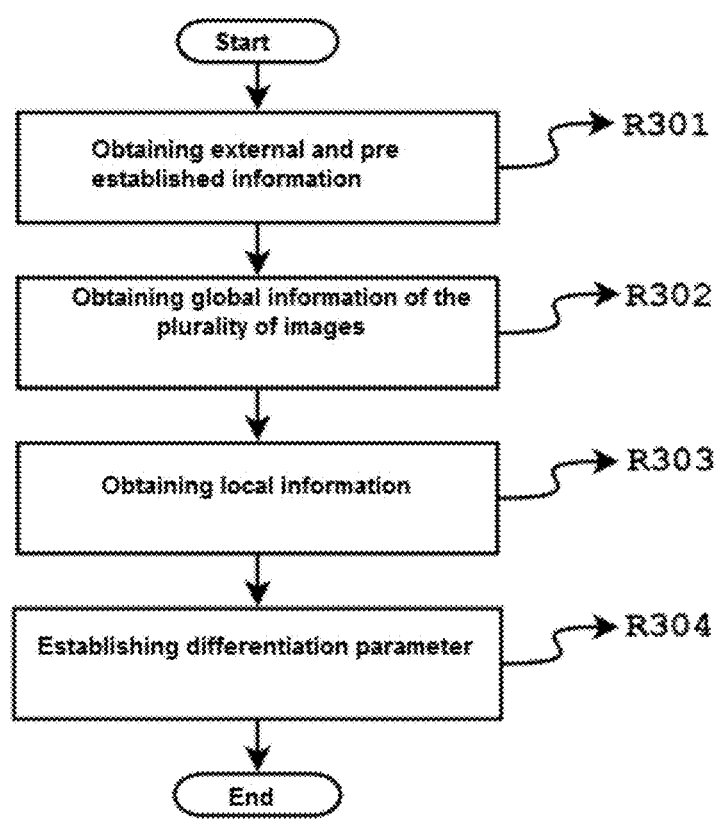
FIG. 3 shows the flow chart that describes in general manner the steps to be followed to set the differentiation parameters.

FIG. 3 shows the flow chart that generally describes the steps to be followed for setting the parameters of differentiation R201. In that chart is considered the obtainment of the necessary information for establishing the differentiation parameters from a set of stages (steps) about the following sources: data previously established (e.g. a data file) at the beginning of the method or external sources (e.g. a user) R301; about the plurality of images or a subset of them, carrying out a global analysis of its voxels R302; about a set of regions within images or in the neighborhood of a subset of voxels, carrying out a local analysis R303. In turn, in the last step R304, differentiation parameters are established from the information collected in the previous steps. Finally, the nature of the information used may correspond to the photometric characteristics of different regions or tissues, such as Hounsfield units used in computed axial tomography images, or other information such as annotations (labels) included in images from other sources.

Although steps R301, R302 and R303 allow to collect a variety of information from the above mentioned sources, and thus allow to establish the differentiation parameters, some embodiment alternatives of the method may consider the inclusion of only a subset of said sources or collect them in a different order. Alternatives where the differentiation parameters are established incrementally are also possible. This means that at the end of step R201 only a subset of the parameters is established, and subsequently the missing parameters are established as information in later steps of the method is collected and analyzed, where it may be more suitable or appropriate to set the remaining parameters.

The differentiation parameters to be established in step R304 comprises those necessary for:

a) Performing pre-processing of the plurality of images;
b) Performing corrections to the regions of the body;
c) Characterizing regions, contours, shapes or textures of the tissues of interest extrinsic R102 and intrinsic R103, of background R107, and other body tissues in the plurality of images;
d) Obtaining the contour R106 that defines the region of differentiation;
e) Establishing the geometry and size of local sampling neighborhoods;
f) Establishing the way how the local sampling of the neighborhoods will be carried out; and
g) Establishing the selection criteria for the differentiation of the extrinsic and intrinsic tissues.

In order to illustrate the nature of the parameters to set in the first step R201 of the method and how said parameters are set, below is an example in which a threshold of separation between two tissues with close photometric characteristics between them is obtained by the histogram analysis. However, in a preliminary manner is very important to emphasize that the histogram object of analysis—as well as any other model for establishing parameters—may be the result of the information obtained in any of steps R301, R302, or R303, or together; the information from an external source can provide, for example, a priori model of characteristic histogram, which together with the information of the frequencies of the voxels coming from a local or global source in the image, will allow to make a more suitable "corrected" histogram to perform the analysis.

Continuing with the example, FIG. 4 provides the representation of a generic histogram of bimodal type R401 for the photometric variable of voxel intensity, where an association between each mode R402 and R403 with a particular tissue present in the image exists. Among the modes exists a separation valley where a partial overlapping of intensities between such modes can be observed. Likewise, a separation threshold R404 allowing defining intervals R405 and R406 for these modes may be observed, which will allow discriminating these associated tissues. This threshold may be obtained through a clustering strategy as k-means or gradient descent R407, among other alternatives.

A differentiation region is defined in the second step of method R202. This step may be accompanied by a pre-processing initial step where the image is filtered and corrected, to further continue with the definition of the differentiation region. Said differentiation region is essential for the method because of the reasons explained below.

Local differentiation of the tissues of interest starts with the assumption according to which all voxels belonging to tissue R105 limiting tissue R102 are labeled in the same manner as the voxels of background R107, or in a more general manner, their label allows differentiating them from the tissues of interest and from any other tissue inside the body region. A way to satisfy the assumption above is labeling the voxels of tissue R105 as background. However, there are several cases where this is not possible, or the obtained result is not very reliable. For example, when it is not possible to photometrically differentiate tissues R104 and R105, and besides these join each other at some point as occurs in locations R110 and R111; or the thickness of tissue R105 shows a considerable variation R114 caused by an acquisition device (such as motion-blur) exceeding any a priori assumption regarding the thickness of said tissue, or in a worst case scenario, when the thickness of tissue R102 does not allow differentiating the separation between tissues R120 and R121 as shown in FIG. 1c. In contrast, voxels inside the regions limited by contours R115 and R122, respectively, comply with the stated assumption, this is, they allow defining a differentiation region for solving the mentioned problems. Finally, it is important to notice that although said differentiation regions do not include the entirety of the voxels of the tissue of interest in the image, the step of differentiation R203 does not demand said condition. Finally, after differentiating the voxels of the tissue of interest in the differentiation region, all the remaining voxels of interest that are not included in said region may be labeled as extrinsic tissue, concluding in this way the differentiation over all the tissue of interest in the image.

Now, the contour R106 limiting the differentiation region may be traced manually by an expert worker or using automatic means taking into account the definition of a parametric contour R501 (FIG. 5a). This parametric contour may be defined using a set of control points R502, wherein said control points may be interpolated through a linear, polynomial or rational function, defining in this way a contour by segments. The location of said control points may be decided based on the identification of the external or internal contour of tissue R522 (FIG. 5c) from the analysis of the global or local photometric characteristics of the voxels in said regions of the image. Also shape analysis, directionality, or local continuity of voxels are alternatives that may be used for that purpose.

Another alternative is, from an initial state for contour R511 (FIG. 5b), changing its shape and position seeking to minimize (or maximize) the value of a pseudo-energy functional (a function that associates real values to a set of functions, for example, line integrals on a vector field), until an equilibrium contour R512 is obtained. Said equilibrium contour is characterized in that small variations to its shape do not produce a reduction of the functional, being the active contours (snakes) and the Level-Sets examples of techniques based on the above principles. Likewise, this initial contour may be configured in several manners. For instance, in a pre-established location in the background R521 so that surrounds the body or inside the body R523 very near to tissue R522. The number of control points R524 to use will depend on the quality required for the contour.

The alternative of using a functional has the advantage of being robust against problems such as: discontinuities in tissue R531 (FIG. 5d), proximity of tissues as in R110 and R111, the occurrence of foreign elements inside of region R102 as seen in R532 and R533, or in general quality problems in the image as a high noise or low contrast. Likewise, said functional may be adjusted based on the photometric characteristics of the body as shown in FIG. 5e, thereby defining a pseudo-energy field as shown in FIG. 5f. Based on this pseudo-energy field, an active contour whose functional is derived from the solution of a differential equation that takes as parameters the initial contour, the pseudo-energy field of the body and a set of external parameters controlling the elasticity and rigidity of the contour may be used.

On the other hand, in the last step of method R203 differentiation of extrinsic and intrinsic tissue is carried out, wherein said step uses the parameters set in step R201 and the differentiation region obtained in step R202. The general flow chart of the differentiation of tissues of interest through local neighborhood evaluation is shown in FIG. 6. Given a set of voxels labeled as tissue of interest inside the differentiation region, one of them R601 is selected, called central voxel. Right after, the voxels inside of the neighborhood local to said central voxel are evaluated R602, thus obtaining a set of quantitative evaluation values. Said set of quantitative values is used to evaluate a group of selection criteria R603, whose parameters were previously established in step R201. If the selection criteria are met, the central voxel is labeled as intrinsic tissue R604, while otherwise, the central voxel is labeled as extrinsic tissue R605. After the differentiation decision is taken, it is verified if the set of voxels of interest pending for labeling is still not empty, so it returns to step R601, or the process is finished.

The evaluation of the local neighborhood of a central voxel may be carried out using a ray tracing technique. It is also possible to carry out such evaluation through the analysis of neighborhoods with diverse pre-established shapes (windows) or using both techniques together. FIG. 7A illustrates a general diagram of the evaluation for extrinsic R701 and intrinsic R702 tissues of interest through ray tracing R703 and R707, from the central voxels R705 and R706 inside of differentiation region R704. Regarding the geometry of rays to trace, there are several alternatives. For example, the angular separation between rays may be uniform, irregular or even random; the amount of rays to trace from a central voxel may be greater or equal to 2, and even said amount of rays may vary depending on the location of the central voxel in the image. Additionally, it is possible to trace curved paths instead of straight paths. Finally, although it has been established that the ray tracing is performed on all voxels of interest, this is not necessary in all cases due to the geometric nature of rays.

FIG. 7b shows the general flow chart describing the steps to be followed to trace the rays and get information of the local neighborhood of a voxel for its evaluation R602. First, a path direction for ray tracing is selected, further establishing the central voxel as its origin R710. Second, the ray tracing is continued in said selected direction until intercepting a new voxel R711, and the information of said voxel is recorded. If the information recorded along the ray tracing meets any of the established stop criteria R712, the stop criteria satisfied by the ray is recorded and its tracing R713 is stopped, otherwise, ray tracing continues. Finally, if there are still rays R714 to trace, is it started again from step R710, otherwise, ray tracing on the central voxel is finished, obtaining a list with the stop criterion information satisfied by each ray traced. The information recorded in said list is interpreted using the selection criteria of intrinsic tissue R603.

An embodiment alternative for performing the local evaluation of the voxels of the tissue of interest using ray tracing is illustrated in FIGS. 7c, 7d and 7e. In FIG. 7c a central voxel R721 located inside of a region of tissue of interest R722 which is mostly defined by tissue R723 is observed. If from the group of traced rays R724, a low amount of them (w or less than w) reached the stop criterion R726 outside the differentiation region R727, then, the central voxel R721 is labeled as intrinsic tissue. On the other hand, in FIG. 7d, a central voxel R734 that is not inside a region mostly enclosed by the R723 tissue is observed. If from the group of traced rays R731, a high amount of them (k or over k, where k is greater than w) reached the stop criterion R732 outside the differentiation region R733, then, the central voxel R734 is labeled extrinsic tissue. Finally, in FIG. 7e, if from the group of traced rays R741, an unrepresentative number of them (greater than w and lesser than k) reached the stop criterion R742 outside the differentiation region, then, the central voxel R744 is labeled as an indeterminate voxel. In the latter case a further analysis is required that completes labeling of indeterminate voxels, for example, one based on the window technique, which is detailed below.

FIG. 7f presents an alternative, called the window technique, to perform the final evaluation of the voxels labeled as indeterminate inside of a neighborhood called final differentiation window, using a final labeling rule. The final differentiation window in which this final evaluation is made, may have any size or shape, and even this may vary depending on the location of the central voxel being evaluated. For example, in FIG. 7f a window formed by the eight voxels adjacent to the indeterminate voxel (the central voxel) is used. In another alternative, said window comprises a larger neighborhood of size 17×17, which allows a more accurate labeling of the central voxel. As rule of final labeling for such alternatives, we have that an indeterminate voxel R751 is labeled as intrinsic tissue, if inside its differentiation window R752 the number of voxels previously labeled as intrinsic tissue R753 is equal to or greater than the number of voxels previously labeled as extrinsic tissue R756. On the other hand, an indeterminate voxel R754 is labeled as extrinsic tissue, if inside its differentiation window R755 the number of voxels previously labeled as extrinsic tissue R756 is higher than the number of voxels previously labeled as intrinsic tissue R753. In yet another alternative, the final evaluation may be performed using windows with multiple shapes, and taking the labeling decision based on the results added on these windows.

In a specific embodiment of the invention, it is disclosed a computer based method to differentiate a tissue of interest, called adipose tissue, between an extrinsic tissue, called subcutaneous adipose tissue (SAT), and an intrinsic tissue, called visceral adipose tissue (VAT), from a plurality of images of the abdominal region (body) of a patient, wherein said method comprises the following steps:

a) Establishing the parameters required to differentiate adipose tissue, including: the segmentation parameters for different tissues of the body, the parameters required to define the differentiation region and the parameters required to perform the differentiation inside of a differentiation region;

b) Removing the abdominal region of the patient from said plurality of images, aimed to the partial removal of the skin, correction, definition and differentiation of the background region and of adipose tissue and of other non-adipose tissues (bone and other soft tissues) as shown in FIG. 9;

c) Segmenting the adipose tissue in said abdominal region as shown in FIG. 10;

d) Defining a differentiation region that includes said segmented adipose tissue in said abdominal region as shown in FIG. 11; and, e) Differentiating as subcutaneous adipose tissue or visceral adipose tissue voxels belonging to said segmented adipose tissue inside of said differentiation region, as shown in FIG. 12.

The extraction of the body is a pre-processing step prior to defining the differentiation region, whose aim is to filter out irrelevant elements in the image and obtain a well-defined region of the body. To perform this second stage, the entirety of the soft tissue (skin, adipose tissue and muscle) is put on a threshold using a predefined range of −500 to 150 Hounsfield units (HU) as shown in the left image of FIG. 9, after which, the image is subjected to a morphological opening operation using a circular structuring element with a radius of 3 voxels, which allows correcting defects in the region and removing foreign elements including the scanner table as shown in the central image of FIG. 9. Subsequently, gaps in the body are filled by an evaluation scheme that uses a variation of the ray tracing technique described above, wherein it is verified that a non-segmented voxel is partially or totally surrounded by segmented voxels, after which continues the application of a morphological closing operator, using again a circular structuring element with a radius of 3 voxels. With this, a mask for this region of the body is obtained, which is used to extract the same from the original image as shown in the right image of FIG. 9, In the third stage, the abdominal adipose tissue is segmented on the image of the extracted body using simple thresholding, using a range provided by the user (the most common range is between −150 and −50 HU) being this the only input parameter required by the method, or obtaining it during the first stage, using histogram analysis or other of the alternatives mentioned above. After this, the gaps present inside the segmented adipose tissue are filled in a similar manner to that described above, but limiting the maximum range of the rays to 7 voxels. With this, small defects in thresholding are corrected, creating uniform regions of adipose tissue. Finally, the step ends with the overlapping of the mask of adipose tissue on the extracted body, thereby obtaining the background, the thresholded regions of adipose tissue and different types of non-adipose tissue.

On the other hand, the fourth step of the method starts with the definition of a differentiation region to guarantee that difficulties in the image such as those described above and illustrated in FIGS. 1b, 1c, 5d, 13b, 13c and 13d, such as the folds of the skin in very obese people and the occurrence of foreign elements, among others, do not affect the differentiation process. Said definition of the differentiation region employs an active contour, which is initialized around the contour of the extracted body in the second stage, as shown in FIG. 5c and left image in FIG. 11.

Active contours, also known as Snakes, are curves models that evolve based on the minimization of their internal energy under an external potential generated from an image. The behavior of the snake is ruled by differential equation (Eq. 1):

$$\alpha x'(s) - \beta x''(s) - \nabla E_{ext} = 0$$

where α controls elasticity of the contour, β the stiffness and ∇Eext is the vector field generated from an external energy potential (coming from image).

The method herein disclosed uses the Gradient Vector Flow (GVF) technique, proposed by Xu and Prince (1997), which allows modeling the external energy generated by the image (the potential of the image) as illustrated in FIG. 5e, to thereby obtain a vector field such as that illustrated in FIG. 5f, which will influence the shape of the Snake. To obtain said vector field, optimization of the functional is carried out (Eq. 2):

$$\varepsilon = \iint \mu (u_x^2 + u_y^2 + v_x^2 + v_y^2) + |\nabla f|^2 |v - \nabla f|^2 dy dx$$

wherein ε is the free energy to minimize, f is the function of the image potential, $\mu$, $\mu_x$ and $\mu_y$ are terms controlling the potential attenuation, and v is the vector field for the image.

On the other hand, the differentiation stage is performed in two iterations. In the first, the evaluation of local neighborhoods identifies voxel candidates for SAT and VAT tissue. In the second, the differentiation is concluded through the analysis of the above result using the window technique.

In the evaluation of local neighborhoods, candidate voxels (SAT and VAT tissues) are identified with high certainty, using a comprehensive method of evaluation of the local neighborhood based on ray tracing on 8 different directions, whose origin is the adipose tissue voxel to be evaluated. With the initialization in each adipose tissue voxel (Eq. 3), the radius of each ray grows iteratively in a conditioned form (Eq. 4), reaching a stop criterion (Eq. 5):

Initialization $$R^k(l^0)_x = x,\ R^k(l^0)_y = y,\ l^0 = 0 \forall (x,y)|(x,y) \in \Im \land S(x,y) = sVal \qquad \text{Eq. 3}$$

Ray Growth $$l^{i+1} = \begin{cases} l^i + 1, & S(R^k(l^i)_x, R^k(l^i)_y) = sVal \\ l^i, & \text{otherwise} \end{cases} \qquad \text{Eq. 4}$$

$$0 \le t,\ (R^k(l^i)_x, R^k(l^i)_y) \in \Im$$

Termination $$l^{i-1} = l^i \Rightarrow V(k) = S(R^k(l^i)_x, R^k(l^i)_y) \qquad \text{Eq. 5}$$

wherein k is the number of the ray to be traced, $R^k(l^i)_x$ and $R^k(l^i)_y$ are the (x,y) coordinates of the k-th beam with length $l^i$, $\Im$ is the set of voxels in the image, S(x,y) is the label of the voxel (x, y), sVal is the label for adipose tissue, and V( ) is a record vector.

Now, the type of adipose tissue to which the voxel (x, y) belongs is identified by evaluating the record vector V( ) using the strong subcutaneous criterion (Eq.6) and strong visceral criterion (Eq. 7):

Strong subcutaneous criterion:

$$SAT(x, y) = \begin{cases} \text{true}, & \sum_{i=1}^{8} I_{backg}(V(i)) \ge 4 \\ \text{false}, & \text{otherwise} \end{cases} \qquad \text{Eq. 6}$$

Strong visceral criterion:

$$VAT(x, y) = \begin{cases} \text{true}, & \sum_{i=1}^{8} I_{backg}(V(i)) \le 2 \\ \text{false}, & \text{otherwise} \end{cases} \qquad \text{Eq. 7}$$

$$I_{backg}(v) = \begin{cases} 1, & v = fVal \\ 0, & \text{otherwise} \end{cases} \qquad \text{Eq. 8}$$

Wherein $l_{backg}$( )(Eq. 8) is a function that returns 1 if the label corresponds to background image, otherwise returns 0.

Finally, voxels that do not meet the strong criteria (only 3 rays reached the background) or indeterminate voxels are evaluated through a final selection criterion or final labeling rule, using information from voxels already differentiated inside a final differentiation window originated in the central voxel being evaluated, following a majority voting scheme.

Finally, voxels classified as SAT and VAT are counted and the result is multiplied by the volume of the voxel in the image, obtaining thus the quantitative measure for SAT and VAT.

Figure 13A:
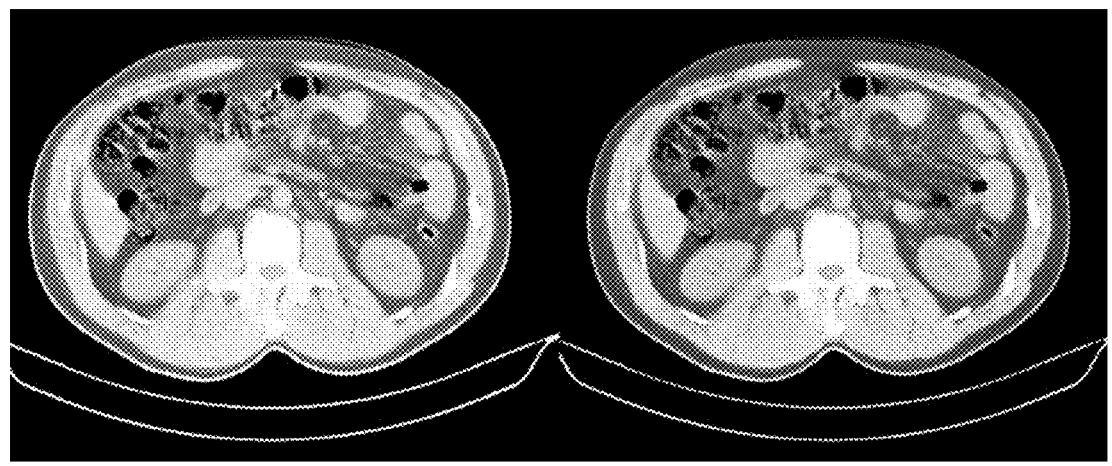
Figure 13B:
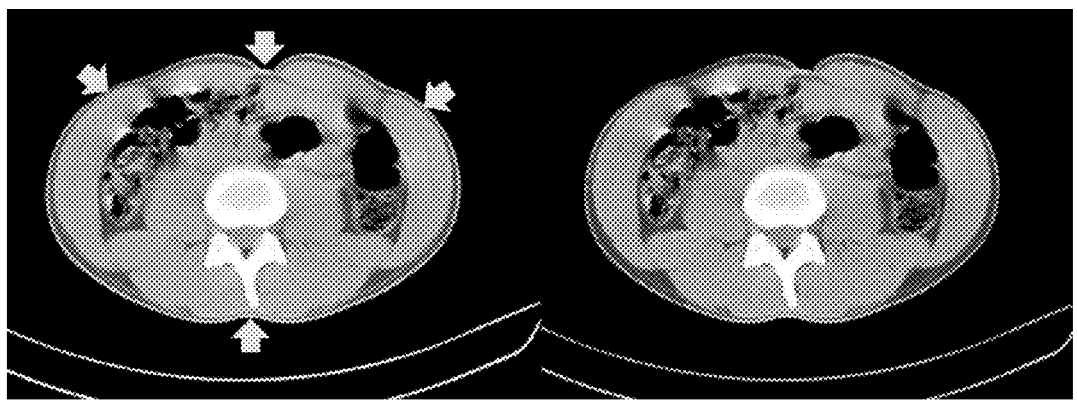
Figure 13C:
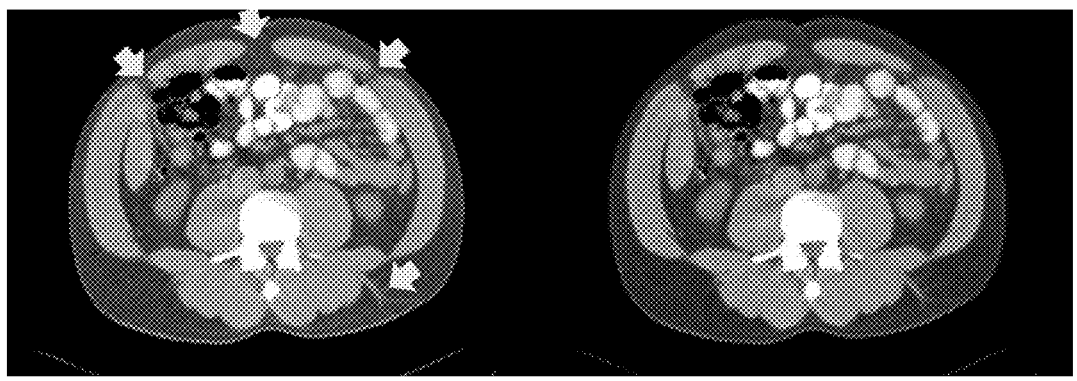
Figure 13D:

FIGS. 13a, 13b, 13c and 13d show examples of results obtained using the specific modality of the method described above on abdominal images by Computed Axial Tomography, where the image on the left is the original cut of the abdominal region and the image on the right corresponds to the result of the differentiation of the tissue of interest (adipose tissue labeled as subcutaneous has been colored blue and adipose tissue labeled as visceral has been colored with red). FIG. 13a shows the results for the image of an individual with a high distribution of visceral tissue. In turn, FIG. 13b shows the result for the image of an individual with a low content of subcutaneous and visceral tissue, wherein the little separation between tissues R104 and R105 can be seen, being this an example of the scenario illustrated in FIG. 1b. FIG. 13c shows the result in an image with little sharpness, where in addition some discontinuities are noticeable in the contour associated with tissue R104 and a foreign element in the lower right part of the body, a fact previously illustrated in the scenario of FIG. 5d. Finally, FIG. 13d shows the status of an image with skin folds, which would cause problems in the differentiation if it was not for the use of a differentiation region.

Now, in yet another embodiment of the invention, the method involves a further stage of filtering small connected components of VAT tissue, which precedes the termination of SAT and VAT tissue segmentation, and in which related components labeled as VAT, whose area is less than a given selection threshold, are re-labeled as a third type of adipose tissue (called intramuscular tissue). Said threshold selection may be calculated by analyzing the histogram of the area of the connected components labeled VAT, wherein said analysis corresponds in turn to the location of a threshold separating the mode of small size connected components and the mode of large size connected components in the histogram, using for this purpose variance-minimization techniques, gradient descent or clustering, such as k-means.

Indeed, what is sought through this additional stage is to differentiate and exclude (filtering) from the VAT segmentation the connected components (or regions) of small size adipose tissue that are not part of this category. In general, these regions may be located in various locations of the retroperitoneal area, usually inside the paravertebral muscles, and more scarcely in oblique musculature, kidneys and epidural region (in the spine core).

These adipose tissue regions are characterized in that their area is lower by several orders of magnitude regarding the regions of adipose tissue of larger size and because they are typically associated to the visceral adipose tissue. Therefore, after VAT segmentation obtained by the method herein disclosed, the steps for obtaining such differentiation and exclusion are:

1. Connected components in the segmented image of VAT tissue are identified, numbered and their area calculated. Thus a list of connected components with their respective area is obtained.
2. Histogram for the frequency of areas of the connected components in the list obtained in step 1 is calculated, hoping to obtain a bi-modal histogram where the smaller area mode represents the small size connected components (which most likely are not VAT) and the higher frequency mode represents larger connected elements (which are most likely VAT).
3. Based on the histogram obtained in step 3, a selection threshold is calculated, which seeks to approximate the optimum separation value between the modes of the histogram. There are several automatic ways to calculate said value: using variance minimization methods like Otsu, gradient descent, or grouping (clustering) and k-means. As parameter in this step a bias value over the selection threshold value obtained may be defined, which allows increasing or reducing (adding or subtracting to the separation value) the degree of exclusion of connected elements.
4. Using the final selection threshold calculated in step 4 differentiation and exclusion of small connected components is carried out. For this, the area of each connected element in the list from step 1 may be compared to the final selection threshold. In the case where the area of the connected component is below said threshold, the connected component is re-labeled with either non-VAT label, or with a new label that symbolizes other adipose tissue. Otherwise, no changes are made to the connected component.

In yet another embodiment of the invention, the method comprises a further step to filter false positives of intestinal contents inside the voxels labeled as VAT. Said stage may be performed before or after making the filtering of small connected components, and consists in the initial application of a differential operator (gradient or Laplacian), of noise or entropy estimation, on the voxels of the original image, currently labeled as VAT, and computing the absolute magnitude of the resulting image, which is thresholded using a previously defined threshold value, thereby labeling only voxels with high magnitude. Then the neighborhood of each voxel labeled as VAT is analyzed using a technique for estimating noise (variance, signal-to-noise ratio, Kullback-Leibler divergence, Shannon entropy or other similar). Finally, the voxel labeled as VAT is re-labeled as non-adipose tissue if the obtained noise estimate is above a previously defined value.

Indeed, this additional stage takes into account characteristics of the texture of the intestinal contents in the computed axial tomography images, so that false adipose tissue voxels in the segmented image of VAT may be identified and eliminated. The steps to perform this additional stage are:

1. Based on the image of the region of interest (the input image in this step is ideally the image of the region of interest, however, the original picture or other image derived from said original image that includes all original intestinal contents may be useful too) a new image called differential image is generated. The differential image is the result of applying a suitable differential operator (or filter), preferably isotropic, as the gradient or Laplacian, or noise or entropy estimation. Finally, the absolute value is calculated at each voxel.
2. Optionally, the differential image may be subject to correction (removal of certain regions), using the segmentation information of adipose tissue in the original image or in another generated during the process. This is with the purpose of eliminating information that could lead to false positives during removal.
3. Differential image is thresholded using a magnitude threshold with a value that is previously defined or automatically calculated (analyzing the histogram according to the filtering method of small connected components), to further segment the image by labeling the voxels whose value exceeds threshold. Interest in high value voxels is that these indicate places where there are great variations in intensity.
4. Finally, removal of false adipose tissue voxels is performed by analyzing neighborhoods on the differential image, which consists of the following selection, estimation and exclusion sub-steps:
   a. Voxels labeled as VAT in the adipose tissue image are selected. In each one of said selected voxels its neighborhood is analyzed within the thresholded differential image. Said neighborhood may have diverse dimensions and shapes, but in a preferred embodiment a circular neighborhood with a radius of at least 5 voxels is used.
   b. The neighborhood is analyzed using a noise (or disorder) estimation model that takes into account the distribution of labeled and unlabeled neighbors inside of the differential image. The preferred estimation model is signal to noise ratio, but other alternatives may be used.

c. If the noise estimation for the neighborhood of a voxel is above a previously defined or automatically determined threshold (following a similar tactic analogue to improvement 1), said voxel is re-labeled as non-VAT (i.e., excluded) in the segmented image of VAT.

Figure 14A:
Figure 14A:
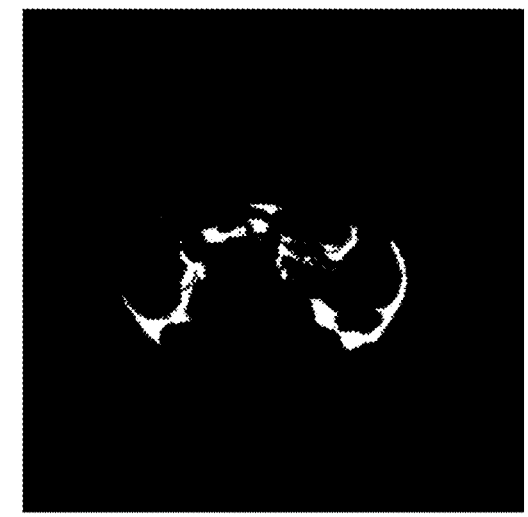
Figure 14B:
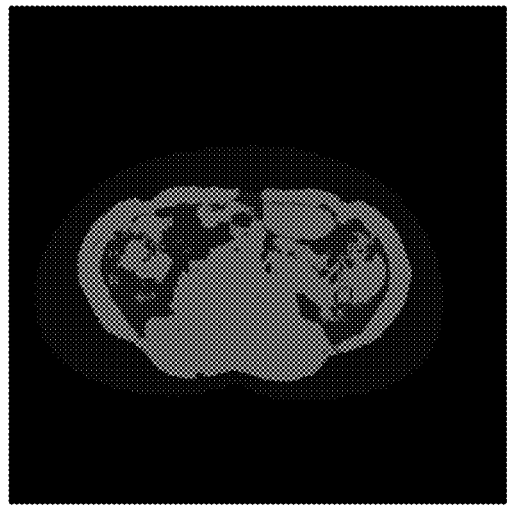
Figure 14B:
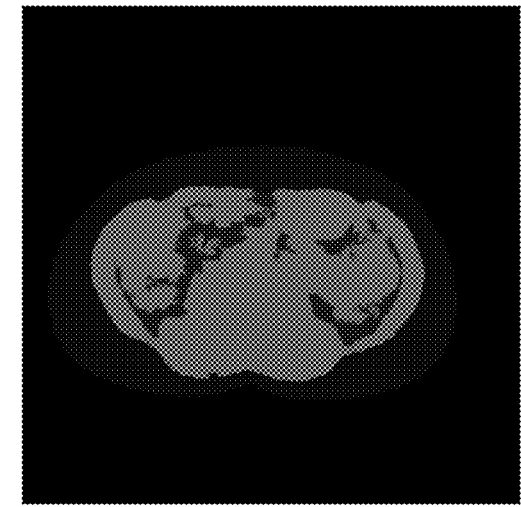
Figure 14C:
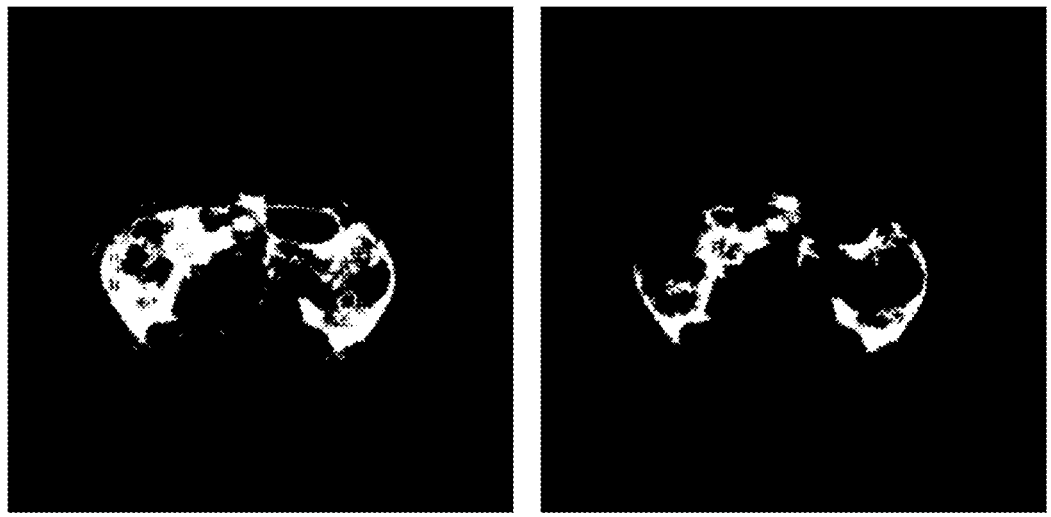
Figure 14D:
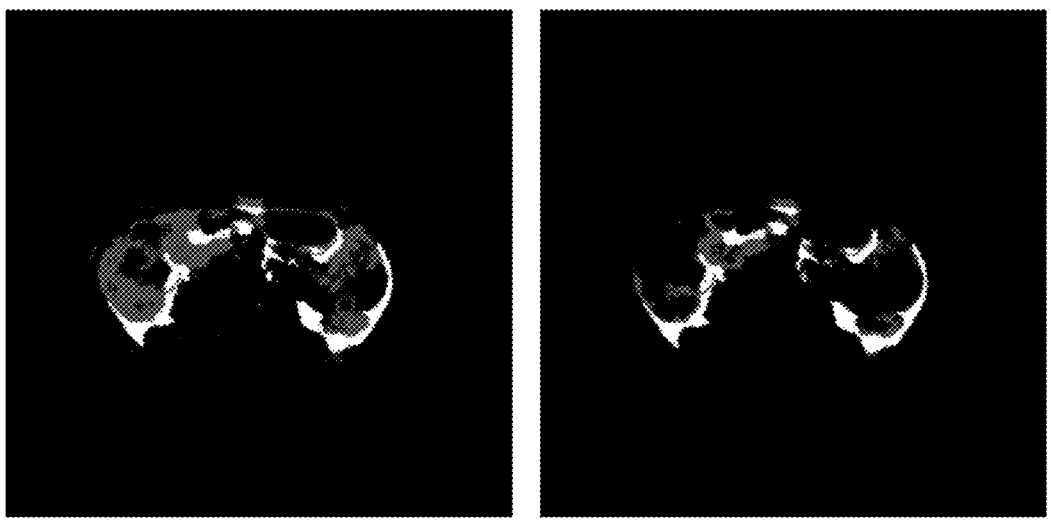

As a comparative example, FIG. 14a presents a case where the image on the left is difficult to differentiate, given the size and the complex form of intestinal contents into the abdomen, while the image on the right shows the gold pattern (the result of a manual segmentation made by 3 experts) corresponding to the visceral adipose tissue. FIG. 14b shows the result obtained using the specific embodiment (left image), and the result obtained using the specific embodiment including the steps of filtering small connected components and filtering false positives from the intestinal content (right image). In turn, FIG. 14c shows visceral adipose tissue regions corresponding to each result of FIG. 14b. Finally, FIG. 14d presents the differences found in the example case, when comparing the gold standard against: the result of the specific embodiment (right image) and the result of the specific embodiment preceded by the filtering steps described above (left image), where the regions in white, red and green correspond to true positives, false positives and false negatives, respectively.

The method of the specific embodiment preceded by the filtering steps described above, was quantitatively evaluated regarding the manual segmentation gold standard using a set of computed axial tomography cuts at the level of the L3 vertebra in 30 patients. Said gold standard was defined as the concordance between manual segmentations of VAT performed in independent and blind fashion by three experts; a voxel was labeled as VAT in the gold standard if and only if the three experts labeled it as VAT. The evaluation results obtained were: $\mu=0.9025$ with $\sigma=0.0512$ for sensitivity, $\mu=0.9856$ with $\sigma=0.0083$ for specificity, $\mu=0.8396$ with $\sigma=0.0560$ for the DICE coefficient, and $\mu=13,1\%$ $\sigma=9.1\%$ for the percentage error between the VAT area of the gold standard and the VAT area estimated by the specific embodiment with filter. Additionally, inter-observer variability was analyzed by measuring the disagreement area between the assessors as a percentage of VAT area according to the gold standard, yielding the following results: $\mu=17.98\%$ with $\sigma=4.33\%$ for disagreement or inter-assessor variability. This indicates that the method provides, on average, a higher precision for estimating the VAT area when compared with the inter-assessor variability observed among experts.

The invention claimed is:

1. A computer-based method for differentiating between two tissues of interest: an intrinsic tissue and an extrinsic tissue, from a plurality of images, comprising the steps of:
   a) establishing parameters required to determine whether an area of the plurality of images corresponds to one or other tissue of interest;
   b) defining a differentiation region in said plurality of images by a parametric contour that follows a pseudo-energy functional calculated using information from said plurality of images and said parameters required to determine whether an area of the plurality of images corresponds to the extrinsic tissue or intrinsic tissue;
   c) differentiating tissues of interest between intrinsic and extrinsic tissue inside the differentiation region defined in b); and,
   d) filtering false positives of the intrinsic tissue and small connected components of the intrinsic tissue in said plurality of images, wherein said step of filtering small components of the intrinsic tissue comprises:
   identifying the connected components in a segmented image of the intrinsic tissue;
   obtaining a histogram for the frequency of areas of the identified connected components;
   calculating a selection threshold based on said histogram of the connected components; and
   changing a label of the connected components whose area is less than said selection threshold in the segmented image of the intrinsic tissue.

2. The method of claim 1, wherein the tissues to be differentiated have similar photometric characteristics but fully or partially border other tissues having different photometric characteristics.

3. The method of claim 1, wherein said plurality of images corresponds to a sequence of two-dimensional reconstructions of signals obtained by a medical imaging device.

4. The method according to claim 1, wherein said parametric contour is an active contour and said pseudo-energy functional corresponds to the solution of a differential equation.

5. The method of claim 1, wherein said stage of establishing differentiation parameters comprises using the photometric characteristics of the different tissues observed in the images.

6. The method according to claim 2 wherein said acquisition device corresponds to a Computed Axial Tomography device, using as photometric characteristic the intensities of the different tissues, as measured in Hounsfield units.

7. The method according to claim 1 wherein the differentiation is carried out by evaluating a local neighborhood of each voxel belonging to said differentiation region, wherein each of said voxels belonging to said differentiation region is a central voxel of its respective local neighborhood.

8. The method according to claim 7, wherein said evaluation of the local neighborhood in each central voxel to be differentiated is performed by evaluating the information contained in intercepted voxels by a set of rays originated at the central voxel to be differentiated and traced at different directions until reaching a stop criterion or until reaching the outside of the differentiation region.

9. The method of claim 8, wherein said set of rays is traced on the plane defined by two-dimensional reconstructions of signals obtained by a medical imaging device.

10. The method of claim 9, wherein said set of rays corresponds to eight rays traced with uniform angular separation of 45 degrees.

11. The method according to claim 8 wherein said stop criterion for each one of said rays corresponds to the interception of the ray and a voxel that does not belong to the tissue of interest.

12. The method according to claim 11, wherein the central voxel is labeled as intrinsic tissue, if k or less than k of the traced rays reached the outside of the differentiation region, or, the central voxel is labeled as extrinsic tissue, if w or more than w of the rays reached the outside of the differentiation region, or otherwise, the central voxel is labeled as indeterminate, wherein k is greater than w.

13. The method of claim 12, wherein the voxels that were labeled as indeterminate are differentiated inside a final differentiation window using a final labeling rule.

14. The method of claim 13, wherein said final differentiation window comprises eight voxels adjacent to the central voxel that was labeled as indeterminate.

15. The method of claim 13, wherein said final differentiation window comprises the voxels of the squared neighborhood of dimensions 17×17, where the central voxel was labeled as indeterminate.

16. The method of claim 15 wherein the final labeling rule, labels the central voxel as intrinsic tissue if inside the differentiation window the number of voxels previously labeled as intrinsic tissue is equal or greater than the number of voxels previously labeled as extrinsic tissue, or otherwise, labels the central voxel as extrinsic tissue.

17. The method of claim 16 wherein the final labeling rule, labels the central voxel as intrinsic tissue if inside the differentiation window the number of voxels previously labeled as intrinsic tissue is greater than three, or otherwise, labels the central voxel as extrinsic tissue.

18. The method of claim 1, which includes an additional step of filling gaps inside the differentiation region, which is performed by tracing a set of rays in different directions with origin at each non-segmented voxel until intercepting an already segmented voxel or a maximum length L, and including said voxel in the segmentation if a subset Q of these rays intercepted an already segmented voxel.

19. The method of claim 18, wherein said set of rays traced with an origin in each voxel of the tissue of interest inside the differentiation region corresponds to eight traced rays with uniform angular separation of 45 degrees.

20. A computer based method for differentiating a tissue of interest, called adipose tissue, between an extrinsic tissue, called subcutaneous adipose tissue (SAT), and an intrinsic tissue, called visceral adipose tissue (VAT), from a plurality of images of the abdominal region of a patient comprising the steps of:
 a) establishing parameters needed for differentiating adipose tissue;
 b) extracting the patient's abdominal region from said plurality of images;
 c) segmenting the adipose tissue in said abdominal region;
 d) defining a differentiation region, that includes said segmented adipose tissue in said abdominal region, by a parametric contour which follows a pseudo-energy function calculated using the information of said plurality of images and said parameters required to determine if a voxel of the plurality of images corresponds to subcutaneous adipose tissue or visceral adipose tissue;
 e) differentiating as subcutaneous adipose tissue or visceral adipose tissue voxels belonging to said segmented adipose tissue inside said differentiation region; and
 f) filtering false positives of the visceral adipose tissue and small connected components of the visceral adipose tissue in said plurality of images,
 wherein said step of filtering small components of the visceral adipose tissue comprises:
  identifying the connected components in a segmented image of the visceral adipose tissue;
  obtaining a histogram for the frequency of areas of the identified connected components;
  calculating a selection threshold based on said histogram of the connected components; and
  changing a label of the connected components whose area is less than said selection threshold in the segmented image of the visceral adipose tissue.

21. The method of claim 20, wherein said plurality of images corresponds to a sequence of two-dimensional reconstructions of signals obtained by a Computed Axial Tomography imaging device.

22. The method of claim 20, wherein said extraction of the abdominal region in the plurality of images comprises the steps of:
 a) segmenting the abdominal region of the patient in the plurality of images;
 b) removing foreign elements included in segmentation and correcting the abdominal region contour;
 d) filling the gaps inside of the segmented abdominal region after removing foreign elements; and
 e) extracting the voxels in the plurality of images belonging to the segmented abdominal region after eliminating foreign elements, removing the skin and filling the gaps.

23. The method according to claim 20, wherein said parametric contour is an active contour and said pseudo-energy function is the solution to a differential equation.

24. The method according to claim 20, wherein the differentiation of the segmented adipose tissue is performed by evaluating a local neighborhood of each voxel belonging to said segmented adipose tissue inside said differentiation region, wherein each of said voxels belonging to said segmented adipose tissue inside said differentiation region is a central voxel of its respective local neighborhood.

25. The method according to claim 24, wherein said evaluation of the local neighborhood in each central voxel to be differentiated is performed by evaluating the information contained in the voxels intercepted by a set of rays originated at the central voxel to be differentiated and traced at different directions until reaching a stop criterion or reaching the outside of the differentiation region.

26. The method of claim 25, wherein said set of rays is traced on the plane defined by two-dimensional reconstructions of the computed axial tomography images.

27. The method of claim 26, wherein said set of rays corresponds to eight rays traced with uniform angular separation of 45 degrees.

28. The method according to claim 25, wherein said stopping criterion for each of said rays corresponds to the interception of the ray and a voxel which does not belong to the adipose tissue.

29. The method of claim 28, wherein the central voxel is labeled as visceral adipose tissue, if k or less than k of the traced rays reached the outside of the differentiation region, or, the central voxel is labeled as subcutaneous adipose tissue, if w or more than w of the rays reached the outside of the differentiation region, or otherwise, the central voxel is labeled as indeterminate, wherein k is greater than w.

30. The method of claim 29, wherein the voxels that were labeled as indeterminate are differentiated inside of a final differentiation window using a final labeling rule.

31. The method of claim 30, wherein said final differentiation window comprises the voxels of the squared neighborhood of dimensions 17×17, where the central voxel was labeled as indeterminate.

32. The method of claim 31 where the final labeling rule, labels the central voxel as visceral adipose tissue if inside the differentiation window the number of voxels previously labeled as visceral adipose tissue is equal or greater than the number of voxels previously labeled as subcutaneous adipose tissue, or otherwise, labels the central voxel as subcutaneous adipose tissue.

33. The method of claim 22, wherein said gap-filling inside of the segmented abdominal region after removing foreign elements is performed by tracing a set of rays in various directions with origin at each non-segmented voxel until intercepting an already segmented voxel or a maximum length L, and including said voxel in the segmentation if a subset Q of said rays intercepted an already segmented voxel.

34. The method of claim 33, wherein said set of rays traced with origin in each non-segmented voxel inside the differentiation region corresponds to eight rays traced with uniform angular separation of 45 degrees.

35. The method of claim 20, wherein said stage of filtering false positives of the visceral adipose tissue comprises:
   a) obtaining a differential image from an image belonging to the plurality of images or from an image derived from said plurality of images;
   b) obtaining a magnitude threshold and labeling voxels in said differential image whose magnitude exceeds the magnitude threshold; and
   c) changing the label of the voxels identified as false positives in the segmented image of VAT tissue, based on the analysis of neighborhoods in the differential image and their labeled voxels.

36. The method according to claim 20, which includes as additional steps filtering false positives of visceral adipose tissue and filtering small connected components of subcutaneous adipose tissue in said plurality of images.

37. The method of claim 35, wherein the operator used to obtain the differential image corresponds to the variance.

* * * * *